United States Patent [19]

Rieber et al.

[11] 4,350,819

[45] Sep. 21, 1982

[54] 1-HYDROXYPYRAZOLE

[75] Inventors: Norbert Rieber, Mannheim; Heinrich Böhm, Neuhofen; Rolf Platz, Mannheim; Werner Fuchs, Ludwigshafen, all of Fed. Rep. of Germany

[73] Assignee: BASF Aktiengesellschaft, Ludwigshafen, Fed. Rep. of Germany

[21] Appl. No.: 284,397

[22] Filed: Jul. 17, 1981

[30] Foreign Application Priority Data

Aug. 20, 1980 [DE] Fed. Rep. of Germany ....... 3031385

[51] Int. Cl.$^3$ .............................................. C07D 231/12
[52] U.S. Cl. ..................................... 548/375; 548/247
[58] Field of Search .......................................... 548/375

[56] References Cited

PUBLICATIONS

Freeman et al., J. Org. Chem. 1969, vol 34(1), pp. 194–198.

Primary Examiner—Alan L. Rotman
Assistant Examiner—N. Harkaway
Attorney, Agent, or Firm—John H. Shurtleff

[57] ABSTRACT

1-Hydroxypyrazole and a process for its preparation by conversion of isoxazolineazoxy compounds at 140°–600° C.

The end products obtainable by the process of the invention are valuable starting materials for the preparation of dyes, crop protection agents and drugs.

1 Claim, No Drawings

1-HYDROXYPYRAZOLE

The present invention relates to 1-hydroxypyrazole and to a process for its preparation by conversion of isoxazoline-azoxy compounds at from 140° to 600° C.

1-Hydroxypyrazole has previously only been known in the form of derivatives having a plurality of substituents on the carbon atoms of the pyrazole ring. Thus, J. Org. Chem., 34 (1969), 194–198 describes the synthesis of trisubstituted 1-hydroxypyrazoles by the following method:

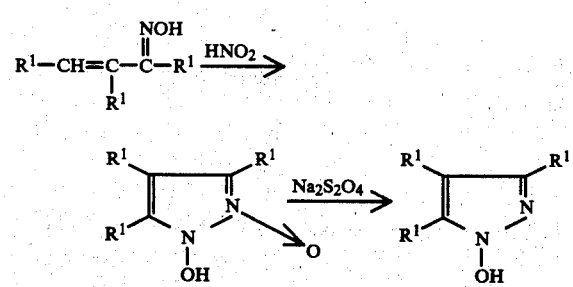

R¹=CH₃ or C₆H₅

We have found that 1-hydroxypyrazole of the formula

Ia mixed with isoxazoles of the formula

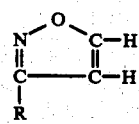

Ib where R is hydrogen or an aliphatic, cycloaliphatic, araliphatic or aromatic radical, is obtained in an advantageous manner by conversion of isoxazoline-azoxy compounds of the formula

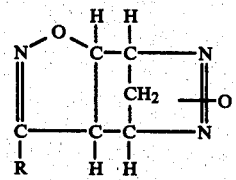

II where R has the above meanings, at from 140° to 600° C.

Further, we have found the novel compound 1-hydroxypyrazole.

Where 2,3-azoxy-6-oxa-7-aza-tricyclo-[5.2.1.0⁵·⁹]-deca-2,7-diene is used, the reaction can be represented by the equation:

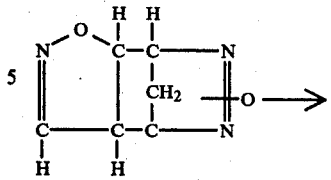

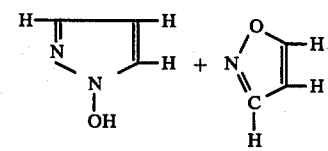

The process according to the invention gives the novel compound 1-hydroxypyrazole, together with isoxazoles, in good yield and high purity, by a simple and economical method. All these advantageous results are surprising in view of the prior art.

Preferred starting materials II and accordingly preferred end products Ia and Ib are those where R is hydrogen, alkyl of 1 to 18, especially 1 to 6, carbon atoms, cycloalkyl of 5 to 8 carbon atoms, aralkyl of 7 to 12 carbon atoms, or phenyl which is unsubstituted or substituted by bromine, fluorine, chlorine and/or alkyl and/or alkoxy of 1 to 4 carbon atoms. The above radicals can additionally be substituted by groups and/or atoms which are inert under the reaction conditions, for example by alkyl and alkoxy, each of 1 to 4 carbon atoms or, in the case of phenyl radicals, by bromine, fluorine or chlorine. The starting materials II can easily be obtained by reacting 2,3,7-triaza-6-oxa-tricyclo-[5.2.1.0⁵·⁹]-deca-2,7-dienes of the formula

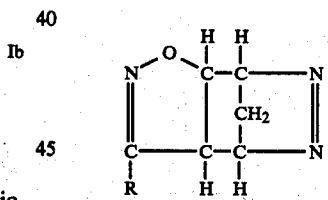

III where R has the above general and preferred meanings, with an organic peroxide, at from −10° to +130° C., preferably from 20° to 100° C., especially from 50° C. to 90° C., under atmospheric or superatmospheric pressure, continuously or batchwise, in the presence or absence of an organic solvent, such as a halohydrocarbon or an ether. The peroxide can be employed in the stoichiometric amount or in excess, the preferred ratio being from 1 to 10, especially from 1 to 1.5, moles of peroxide per mole of starting material. The starting materials III can in turn be prepared easily by, in a first step, reacting a nitrile oxide of the formula

 R¹CNO IV where R¹ has the above general and preferred meanings, with an N,N'-dicarbalkoxy-2,3-diaza-bicyclo-[2,2,1]-hept-2-ene of the formula

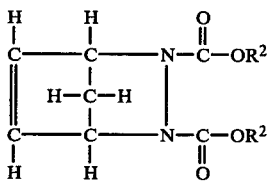

where the radicals $R^2$ can be identical or different and each can be hydrogen or an aliphatic radical, and then, in a 2nd step, subjecting the resulting N,N'-dicarbalkoxy-isoxazolino compounds of the formula

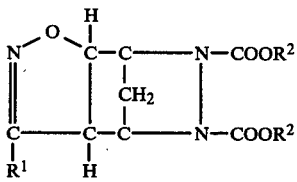

where $R^1$ has the above meanings, to hydrolysis, decarboxylation and oxidation, by conventional methods, to give the starting compound III.

The starting compounds IV are easily obtainable by the method described in Houben-Weyl, Methoden der Organischen Chemie, volume 10/3, pages 841–853, for example by dehydrogenating aldoximes, or from hydroxamic acid derivatives or nitrolic acids. The starting compounds V are obtained, for example, by reacting cyclopentadiene with a dimethyl azodicarboxylate by the process described in Ann. 443 (1925), 242–262.

The oxygen of the azoxy group can be bonded to either nitrogen atom of the azo group. Accordingly, the starting material II can be a pure isomer

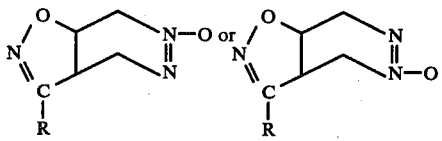

or can, advantageously, be the isomer mixture as obtained from the preparation of the compound.

Examples of suitable starting materials II are 2,3-azoxy-6-oxa-7-aza-tricyclo-5.2.1.0^{5.9}-deca-2,7-diene and its homologs in which the 8-position is substituted by methyl, ethyl, propyl, isopropyl, butyl, isobutyl, sec.-butyl, tert.-butyl, cyclohexyl, cyclopentyl, benzyl, phenyl, 2'-chlorophenyl, 3'-chlorophenyl, 4'-chlorophenyl, 2'-methylphenyl, 3'-methylphenyl, 4'-methylphenyl, 2'-methoxyphenyl, 3'-methoxyphenyl, 4'-methoxyphenyl, 2'-ethylphenyl, 3'-ethylphenyl, 4'-ethylphenyl, 2'-ethoxyphenyl, 3'-ethoxyphenyl or 4'-ethoxyphenyl.

The reaction is carried out at from 140° to 600° C., preferably from 150° to 500° C.; in the case of starting materials II, where R is hydrogen or an aliphatic, cycloaliphatic or araliphatic radical the temperature used is advantageously from 200° to 600° C., preferably from 250° to 500° C., especially from 300° to 450° C., whilst in the case of starting materials II where R is an aromatic radical, it is advantageously from 140° to 200° C., preferably from 150° to 190° C., especially from 160° to 180° C. The reaction is carried out under atmospheric, superatmospheric or reduced pressure, batchwise or continuously, in the presence of organic solvents which are inert under the reaction conditions or advantageously-if only for economic reasons—in the absence of an organic solvent.

The reaction can for example be carried out as follows: the starting material II is kept at the reaction temperature for from one second to 21 hours. The end products Ia and Ib are then isolated from the reaction mixture in a conventional manner, for example by fractional distillation or condensation, extraction or crystallization.

The end products Ia and Ib obtainable by the process of the invention are valuable starting materials for the preparation of dyes, crop protection agents and drugs. 1-Hydroxypyrazole can easily be converted to pyrazole, by a method similar to that described in J. Org. Chem., loc. cit., by reduction with zinc, or by hydrogenation in the presence of Raney nickel. Regarding the use of the product, reference may be made to the above publication and to Ullmanns Encyklopädie der technischen Chemie, volume 8, pages 498–500. The use of pyrazole as a starting material for the preparation of herbicides is described in German Published Application DAS 2,648,008.

In the Examples which follow, parts are by weight.

EXAMPLE 1

97 parts of 8-methyl-2,3-azoxy-6-oxa-7-aza-tricyclo-[5.2.1.0^{5.9}]-deca-2,7-diene are passed, in the course of 2 hours, at 455° C. and 5 mbar, through a tubular reactor packed with 300 parts of quartz rings. The reaction mixture is subjected to fractional condensation in 2 receivers. In the first receiver, which is cooled to 5° C., 47 parts (97% of theory) of 1-hydroxypyrazole, of melting point 75° C. (after recrystallization from naphtha), are obtained. The second receiver, cooled to −70° C., contains 46 parts (95% of theory) of 3-methylisoxazole of boiling point 117° C.

EXAMPLE 2

100 parts of 8-phenyl-2,3-azoxy-6-oxa-7-aza-tricyclo-[5.2.1.0^{5.9}]-deca-2,7-diene are heated at 170° C. for 20 hours. The reaction mixture is then distilled under 5 mbar (at which pressure the boiling point is 50°–120° C.). 200 parts of water are added to the distillate and the mixture is extracted twice with 100 parts of petroleum ether. The two phases are separately concentrated in a rotary evaporator at 10–20 mbar and 20°–40° C. bath temperature; the water phase gives 25 parts (68% of theory) of 1-hydroxypyrazole, of melting point 75° C., and the organic phase gives 55 parts (87% of theory) of 3-phenyl-isoxazole, of boiling point 130° C./20 mbar.

EXAMPLE 3

10 parts of 8-(p-chlorophenyl)-2,3-azoxy-6-oxa-7-aza-tricyclo-[5.2.1.0^{5.9}]-deca-2,7-diene are heated for 10 hours at 170° C. and the material is then sublimed at 10–20 mbar and a bath temperature of up to 160° C. According to NMR analysis, 2.85 parts (89% of theory) of 1-hydroxypyrazole, of melting point 75° C., and 6.33 parts (93% of theory) of 3-(p-chlorophenyl)-isoxazole, of melting point 78° C., are obtained. The melting points are determined after separating the mixture by column chromatography on silica gel (with petroleum ether/ether as the mobile phase).

EXAMPLE 4

35 parts of 8-ethyl-2,3-azoxy-6-oxa-7-aza-tricyclo-[5.2.1.0^{5.9}]-deca-2,7-diene are passed in the couse of 1.5 hours, at 410° C. and 65 mbar, through a tubular reactor packed with 300 parts of quartz rings. The reaction mixture is condensed in a receiver at −60° C. Distillation of the condensate gives 14.6 parts (78% of theory) of 3-ethyl-isoxazole, of boiling point 133° C., and 14.8 parts (91% of theory) of 1-hydroxypyrazole, of melting point 75° C. (after recrystallization from naphtha).

EXAMPLE 5

25 parts of 8-isopropyl-2,3-azoxy-6-oxa-7-aza-tricyclo-[5.2.1.0^{5.9}]-deca-2,7-diene are converted in the course of one hour by the method described in Example 2. Distillation of the condensate gives 10.1 parts (94% of theory) of 1-hydroxypyrazole, of melting point 75° C. (after recrystallization from naphtha) and 13.1 parts (92% of theory) of 3-isopropyl-isoxazole, of boiling point 144° C.

EXAMPLE 6

43 parts of 8-tert.-butyl-2,3-azoxy-6-oxa-7-aza-tricyclo-[5.2.1.0^{5.9}]-deca-2,7-diene are converted in the course of 1.5 hours by the method described in Example 2. Distillation of the condensate gives 17 parts (93% of theory) of 1-hydroxypyrazole, of melting point 75° C. (after recrystallization from naphtha) and 23 parts (93.5% of theory) of 3-t-butylisoxazole, of boiling point 75° C./40 mbar.

EXAMPLE 7 (USE EXAMPLE)

One part of 1-hydroxypyrazole is dissolved in 10 parts of 32 percent strength by weight hydrochloric acid and 5 parts of zinc are added, a little at a time, at 60° C. After 16 hours, the reaction solution is neutralized with sodium hydroxide solution and extracted with ether. On concentrating the ether phase, 0.6 part of pyrazole (75% of theory), of melting point 68° C. (after recrystallization from naphtha), is obtained.

EXAMPLE 8 (USE EXAMPLE)

One part of 1-hydroxypyrazole and 0.3 part of Raney nickel in 10 parts of methanol are reacted with hydrogen under 50 bar for 5 hours at 100° C. The catalyst is filtered off and rinsed with methanol, and the solution is evaporated. 0.75 part of pyrazole (93% of theory), of melting point 68° C. (after recrystallization from naphtha), is obtained.

We claim:
1. 1-Hydroxypyrazole of the formula

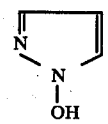

Ia

* * * * *